United States Patent
Takizawa et al.

[19]

[11] Patent Number: 6,063,067

[45] Date of Patent: May 16, 2000

[54] DISPOSABLE DIAPER AND METHOD OF FOLDING AND FASTENING THE SAME AS WASTE

[75] Inventors: Toshiaki Takizawa; Masashi Doi; Tsuyoshi Minato, all of Toyama-ken, Japan

[73] Assignee: YKK Corporation, Tokyo, Japan

[21] Appl. No.: 09/122,084

[22] Filed: Jul. 24, 1998

[30] Foreign Application Priority Data

Jul. 25, 1997 [JP] Japan ..................................... 9-200340

[51] Int. Cl.$^7$ ...................................................... A61F 13/15
[52] U.S. Cl. ...................... 604/386; 604/364; 604/385.1; 604/386; 428/350; 24/452
[58] Field of Search .................................... 428/350, 100; 24/442–452, 306; 604/385.1, 386, 389, 390, 391, 364

[56] References Cited

U.S. PATENT DOCUMENTS

| | | | |
|---|---|---|---|
| H1340 | 7/1994 | Yetter et al. | 604/376 |
| 3,860,003 | 1/1975 | Buell | 128/287 |
| 4,338,800 | 7/1982 | Matsuda | 66/194 |
| 4,985,024 | 1/1991 | Sipinen . | |
| 5,071,414 | 12/1991 | Elliott | 604/385.1 |
| 5,230,851 | 7/1993 | Thomas | 264/145 |
| 5,360,270 | 11/1994 | Appeldorn et al. . | |
| 5,368,549 | 11/1994 | McVicker . | |
| 5,681,299 | 10/1997 | Brown | 604/364 |
| 5,722,966 | 3/1998 | Christon et al. | 604/364 |

FOREIGN PATENT DOCUMENTS 0 768 074   4/1997   European Pat. Off. .

*Primary Examiner*—John G. Weiss
*Assistant Examiner*—Carie Mager
*Attorney, Agent, or Firm*—Hill & Simpson

[57] ABSTRACT

A disposable diaper has a pair of first surface fastener members supported by a rear flap of a diaper body and a second surface fastener member supported by a front flap of the diaper body. The first and second surface fastener members have first and second engaging elements; the first and/or second engaging elements are made of water-soluble resin. After approximately 1/3 to 2/5 of the diaper body on the side of the rear flap is folded inwardly, the diaper body is wound into a roll toward the front flap, and then the water-soluble resin of the first and/or second engaging elements is dissolved with water. Then the first surface fastener members are pressed against the second surface fastener member to fasten the diaper body in roll as waste.

11 Claims, 5 Drawing Sheets

DISPOSABLE DIAPER AND METHOD OF FOLDING AND FASTENING THE SAME AS WASTE

BACKGROUND OF THE INVENTION

1. Field of the Invention

The present invention relates to a disposable diaper and a method of folding and fastening a disposable diaper as waste, and more particularly to a disposable diaper adapted to be fastened in a compactly folded form as waste.

2. Description of the Related Art

In recent years application of disposable diapers whose chief materials are non-woven cloth or paper has been on the increase for either infants or aged persons. Among various diapers, paper diapers for infants or sick persons are the typical products. In these conventional diaper products, a diaper body is composed of outer and top sheets and a liquid absorbing layer intermediate between the outer and top sheets; in use, the diaper body is detachably attached to the user by a fastening member.

In the meantime, the cherished demands of the users vary from good in liquid absorption, ventilation, liquid-leakage proofness and texture, which are fundamental requirements to the diaper products, to rational price and simple structure, easy attachment and removal at any time except in use, and easy sanitary handling without losing its shape after being folded in a compact form as waste.

The common problem with this conventional type diaper is that since the used diaper is merely rolled as waste, the rolled diaper would tend to lose its shape to occasionally allow leak of excrement, which is not sanitary to handle the used diaper as waste.

SUMMARY OF THE INVENTION

It is therefore an object of the present invention to provide a disposable diaper which is simple in structure and easy to fasten in folded form by a simple operation and also a method of folding and fastening such a disposable diaper as waste.

According to a first aspect of the invention, the above object is accomplished by a disposable diaper comprising a diaper body having a front flap and a rear flap. The diaper further comprises a surface fastener composed of a pair of first surface fastener members (ex. male surface fastener member), and second surface fastener member(ex. female surface fastener member). The first surface fastener members are supported by the rear flap and extending laterally in opposite directions from the rear flap and the second surface fastener member is supported by the front flap. Each of the first surface fastener members consists of a first substrate sheet and a multiplicity of first engaging elements (ex. male engaging elements) standing on the front and/or the rear surface of the first substrate sheet. The second surface fastener member consists of a second substrate sheet and a multiplicity of second engaging elements (ex. female engaging elements) standing on the front surface of the second substrate sheet for engagement with the first engaging elements. The first and/or second engaging elements are made of water-soluble resin.

If a hybrid type surface fastener having on its front surface male and female engagement elements in mixture is used as each of the first and second surface fastener members, the first and second surface fastener members have a common structure.

Though there is no significant difference in attaching and removing operation from the conventional disposable diaper, the disposable diaper of the present invention can be fastened in a very compactly folded and rolled form as waste without leakage of excrement, thus making it sanitary to handle as waste.

According to a second aspect of the invention, there is provided a first method to fold and to fasten the above-described diaper of the present invention as waste. The method comprises the steps as follows. Firstly, fold approximately ⅓ to ⅔ of the diaper body on the side of the rear flap inwardly. Secondly, wind the diaper body into a roll with the folded rear flap as a core toward the front flap. Thirdly, dissolve the water-soluble resin of the first engaging elements of the first surface fastener members projecting from opposite ends of the roll of the diaper body and/or the second engaging elements of the second surface fastener member with water. Finally, press the first surface fastener members against the second surface fastener member to fasten the diaper body in roll.

According to a third aspect of the invention, there is provided a second method to fold and to fasten the above-described diaper of the present invention as waste. The method comprises the steps as follows. Firstly, fold approximately ⅓ to ⅔ of the diaper body on the side of the front flap inwardly. Secondly, wind the diaper body into a roll with the folded front flap as a core toward the rear flap. Thirdly, dissolve the water-soluble resin of the first engaging elements of the first surface fastener members projecting from opposite ends of the roll of the diaper body with water. Finally, press the first surface fastener members against a back sheet of the diaper body to fasten the diaper body in roll.

When folding and fastening the used diaper, the necessary number of windings of the diaper into a roll depends on the amount of excrement. At this time, leakage of the excrement tends to happen with the conventional diaper. While with the diaper of the present invention, partly since the second surface fastener member has an adequate size and partly since the first surface fastener member has on its front and/or rear surface a multiplicity of male engaging elements, it is possible to fasten the folded and rolled diaper body by pressing the male surface fastener against the female surface fastener surface a multiplicity of male engaging elements, it is possible to fasten the folded and rolled diaper body pressing the male surface fastener against the female surface fastener member, irrespective of the number of windings of the diaper body. Further, since each of the front and rear flaps has a pair of lateral wings, the opposite ends of the roll can be closed with them. Therefore, it is possible to handle the used diaper very sanitarily without leakage of excrement from the diaper body even when the excrement moves over a pair of leak-barrier taper of the diaper body.

From and economical view point, it is preferable that the male engaging elements are molded of synthetic resin on the substrate sheet. As an alternative, the male engaging elements may be monofilaments woven or knitted of the woven or knitted substrate sheet.

The female engaging elements of the female surface fastener member are usually pile of a woven or knit cloth substrate sheet. Alternatively, in view of recent miniaturization of companion male engaging elements may be pile on a non-woven cloth should by no means be limited to the pile projecting from the front surface of a non-woven cloth formed or mutually entangled fibers; the pile may mean also the interstices formed in a non-woven cloth whose interstices are relatively large. Further, the substrate sheet of the male and/or female surface fastener member may be made of water-soluble resin. Or at least one part of the diaper body may be made of water-soluble resin.

DETAILED DESCRIPTION OF THE PREFERRED EMBODIMENTS

The preferred embodiments and examples of the present invention will now be described in detail with reference to the accompanying drawings.

Figure 1:
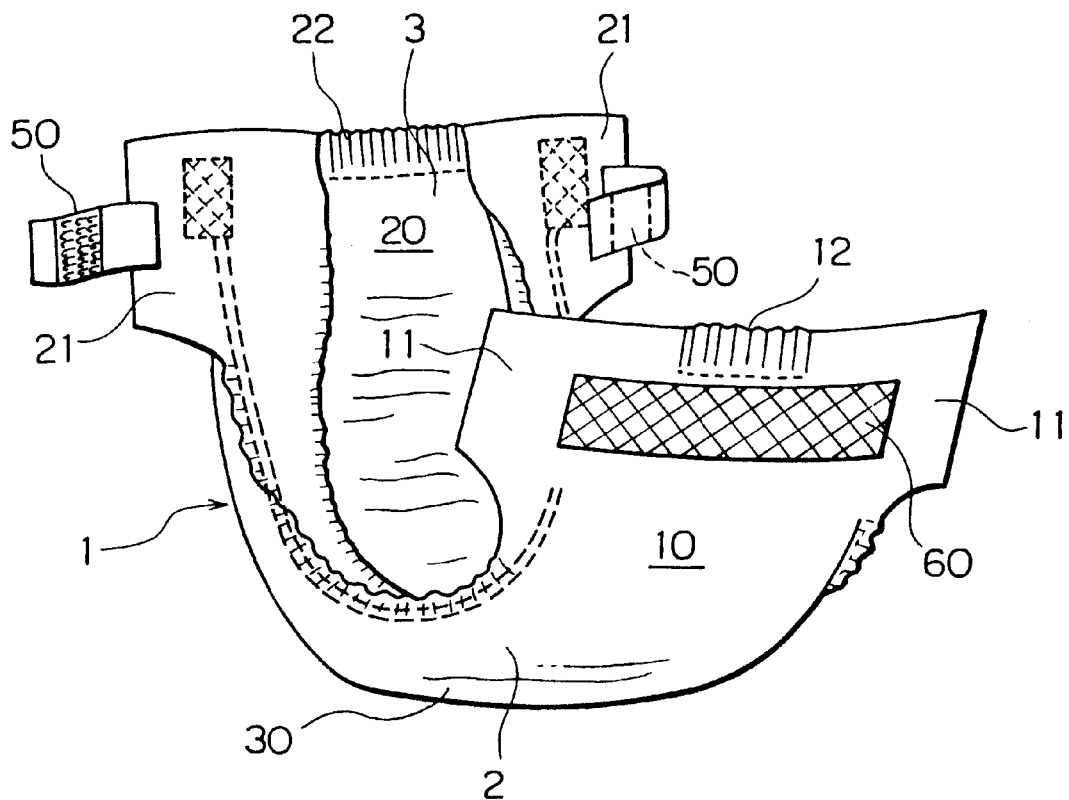
FIG. 1 is a perspective view showing a disposable paper diaper, in an opened posture before use, according to a typical embodiment of the present invention.
Figure 2:
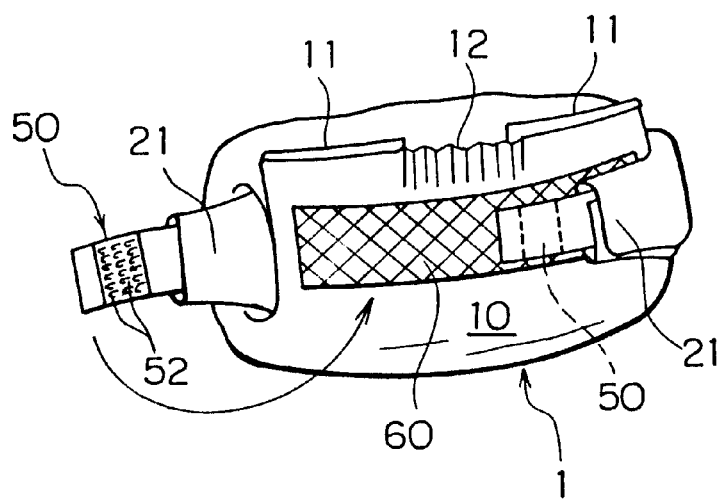
FIG. 2 is a perspective view showing the paper diaper of FIG. 1 when fastened in folded form as waste according to a first method.

FIG. 1 is a perspective view showing an infant-use disposable paper diaper, in an opened posture before use, according to a typical embodiment of the present invention. FIG. 2 is a perspective view showing the same diaper when fastened in folded form as waste according to a first method (described later). It will be understood from the following description that the present invention should by no means be limited to the infant-use disposable diaper. It may be applied also to the adult-use disposable diaper with the same advantageous result.

The diaper basically comprises a diaper body 1 to be attached to the user's body, and a surface fastener (described below) for holding the diaper body 1 to the user. The diaper body 1 has a front flap 10, a rear flap 20, and a crotch portion 30 extending between the front and rear flaps 10, 20. The entire diaper body 1 is composed of a back sheet 2, a top sheet 3, and a non-illustrated liquid absorbing pad. When the diaper body 1 is attached to the user's body, the back sheet 2 comes to the outside and the top sheet 3 comes to the inside. The liquid absorbing pad is sandwiched between the outer and top sheets 2, 3. The outer and top sheets 2, 3 are substantially identical in entire shape. When they are joined together in laminate, the whole diaper body 1 shows a generally H shape that is turned 90° with a pair of wings 11, 21 extending laterally in opposite directions from the front and rear end of a central rectangle respectively. The non-illustrated liquid absorbing pad is held between the outer and top sheets 2, 3 and extends throughout their entire areas except their peripheral edges and the wings 11, 21. The peripheral edges of the outer and top sheets 2, 3 are joined together by a suitable means such as adhesive or high-frequency fusion.

The back sheet 2 must be water-resistant. It may be a simple synthetic resin film such as polyethylene or polyolefin; yet it is preferable that its outer surface has a texture like an ordinary cloth. For example, a multiplicity of small dimples may be formed on the film, or the synthetic film as mentioned may be laminated over and joined with the rear surface of a non-woven cloth preferably at a multiplicity of spots or lines by a suitable joining means such as adhesive, high-frequency fusion or thermal fusion. Also preferably the film is ventilative.

The top sheet 3 may be made of a hydrophilic or hydrophobic material. Because the top sheet 3 must allow liquid to pass through and from an economical point of view, it is preferable to use a non-woven cloth of synthetic fibers. The material of the synthetic fibers is exemplified by polyethylene, polypropylene, polyester and nylon. Further, the top sheet 3 may be elastic; for example, such a non-woven cloth is produced by simultaneously spinning two kinds of synthetic resins different in contraction with hot water as composite fibers and then by treating the result composite fibers with hot water. During this production, the composite fibers and a predetermined quantity of synthetic resin powder having a melting point lower than that of the fibers are uniformly mixed to form a web. Then, the web is heated at a temperature higher than the melting point of the synthetic resin powder and lower than that of the fibers to melt the synthetic resin powder and, at the same time, the molten synthetic resin of the powder is collected at intersections of the fibers by utilizing a capillary phenomenon. Whereupon the molten synthetic resin is cooled to join the fibers at their intersections, thus completing the production of the non-woven cloth. As a simpler alternative, a predetermined quantity of adhesive may be uniformly sprayed over the fiber web to obtain a desired non-woven cloth. In this case, a suitable quantity of solvent is added to the adhesive.

The liquid absorbing pad may be a felt of cellulose fibers or hydrophilic synthetic fibers such as polyvinyl alcohol. Alternatively, liquid-absorbent gel grains or fibers may be mixed in such felt. The liquid-absorbent gel is exemplified by an inorganic substance such as silica gel and an organic composition such as a cross-link polymer. Further, in order to hold liquid and also to stably retain the liquid-absorbent substance inside, the liquid-absorbing pad is preferably a laminate form composed of a plurality of thin-film fiber webs.

In addition to the foregoing fundamental structure, the disposable diaper of the present invention has a primary characteristic feature as follows.

As shown in FIG. 1, a pair of first surface fastener members 50 of the surface fastener are attached one to each of the two wings 21, which extend laterally in opposite directions from opposite lateral sides of a rear waist 22 of the rear flap 20. And a rectangular second surface fastener member 60 is attached to a front waist 12 of the front flap 10 throughout its substantially entire area.

Figure 3:
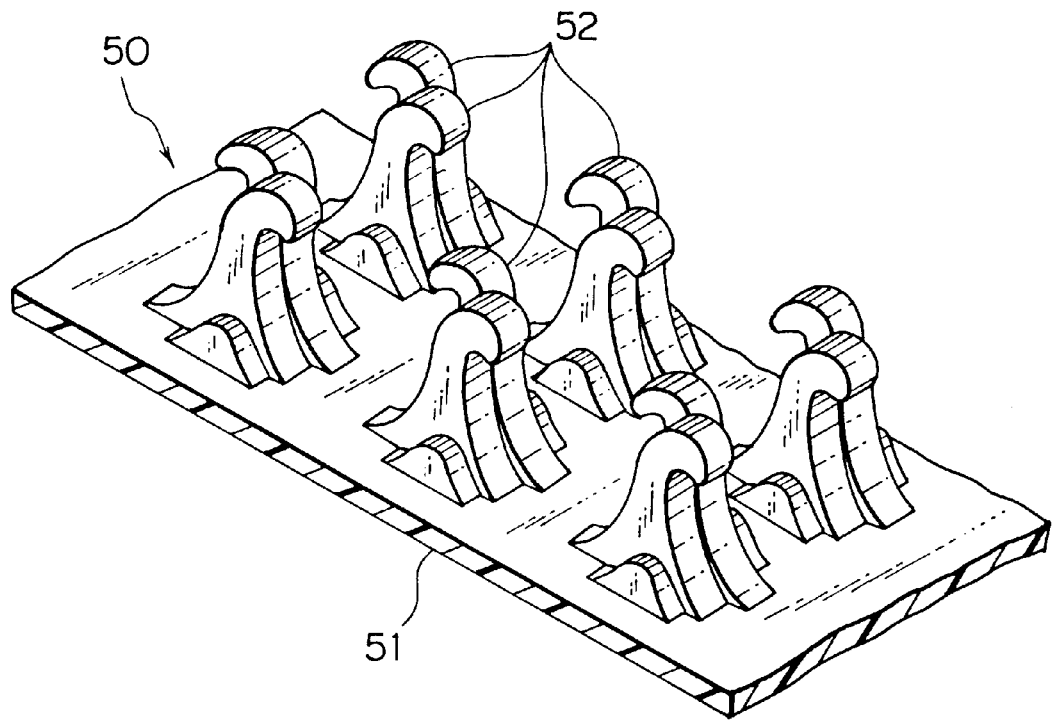
FIG. 3 is a fragmentary perspective view of one example of male surface fastener member to be used in the diaper of FIG. 1, in which member, male engaging elements are integrally molded on a substrate sheet.
Figure 4:
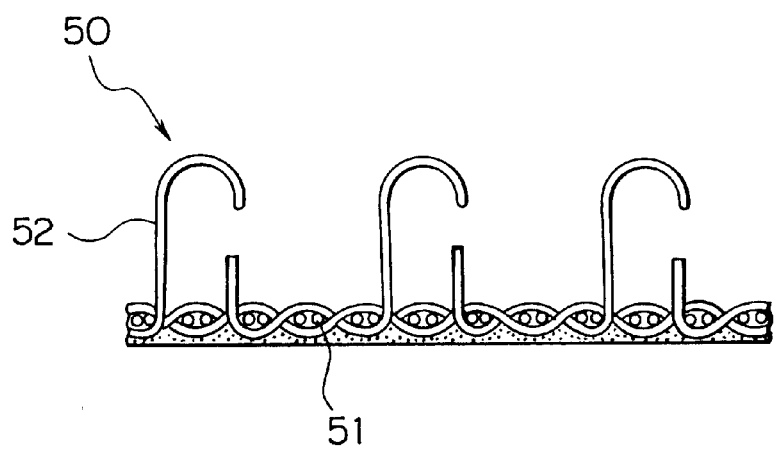
FIG. 4 is a fragmentary cross-sectional view of another example of male surface fastener member to be used in the diaper of FIG. 1, which member is formed of fibers.

In the illustrated embodiment, the first surface fastener member 50 is a molded male surface fastener member in which a plurality of hook-shaped male first engaging elements 52 are molded of a thermoplastic synthetic resin on a first substrate sheet 51 of the same resin as shown in FIG. 3. If an economical view point can be ignored, the first surface fastener member 50 may be a woven or knit male surface fastener member whose male engaging elements 52 are in the form of monofilaments woven or knitted in a woven or knit cloth of fibers as shown in FIG. 4. In the molded male surface fastener member 50, the male engaging members 52 should by no means be limited to the hook shape and may be mushroom-shaped. Further, the male engaging members 52 may be formed on opposite surfaces of the substrate sheet 51.

Although it is not illustrated in the drawings, mushroom-shaped male engaging elements may be molded on the rear surface of the same substrate sheet 51 when molding the hook-shaped male engaging elements 52 on the front surface of the substrate sheet 51. In this alternative, the male surface fastener member 50 is a unitary molded form rather than a two-film laminate form.

As shown in FIG. 1, the second surface fastener member 60 is a rectangular female surface fastener member. It i s attached to substantial center of the front waist 12 of the front flap 10 using adhesive or by fusion. The second surface fastener member 60 comprises a second substrate sheet 61 and a plurality of second engaging elements 62. In the female surface fastener member 60, the engaging elements 62 are usually pile of a woven or knit cloth substrate sheet 61. Alternatively, in view of recent miniaturization of companion male engaging elements, adequate engaging strength can be secured by forming the corresponding part of the back sheet 2 with a non-woven cloth.

The most important feature of the disposable diaper of the present invention is that the male and/or female engaging elements 52, 62 (FIGS. 3 to 5) of the first and/or second surface fastener member 50, 60 are made of water-soluble resin. This water-soluble resin sticks to a surface of a companion article by applying a suitable solvent such as water or alcohol solution. For the substance of the water-soluble resin, a water-soluble resin having a hydrophilic group, such as a hydroxyl group, a carboxyl group or a sulfonic group, and also having a moldability and a suitable degree of softness and hardness will suffice. This substance is exemplified by polyvinyl alcohol, decomposed polyvinyl alcohol, polyacrylic acid, polyethylene oxide, CMC and gum; among them, decomposed polyvinyl alcohol is most preferable in view of moldability and adhesion after dissolution.

Figure 6:
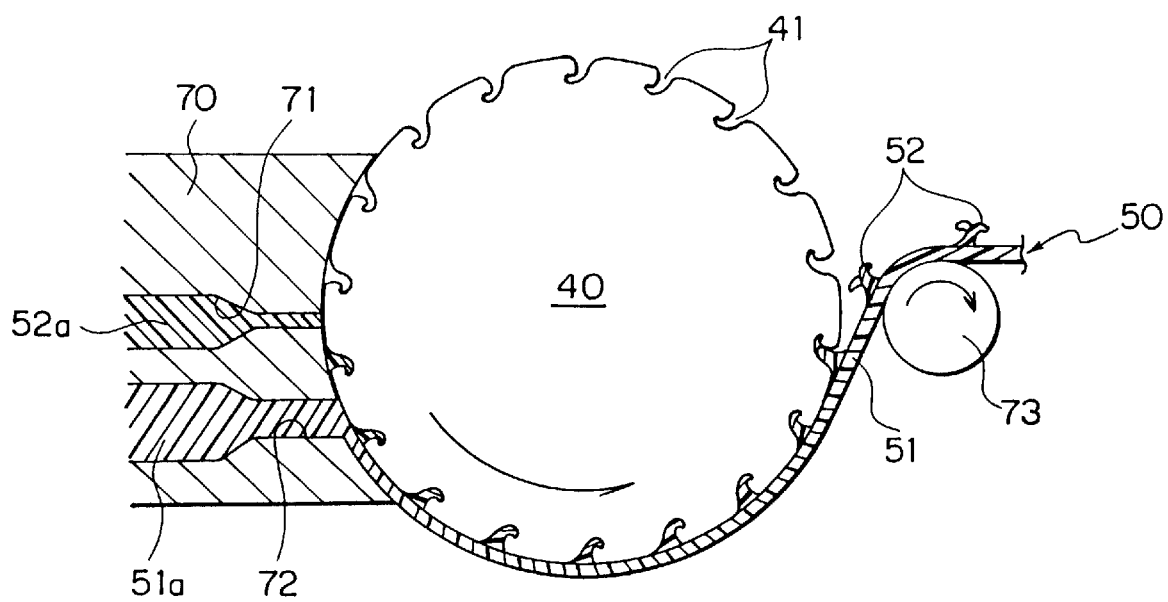
FIG. 6 is a diagram showing one example of molding process for the male surface fastener member.

The above-mentioned molded male surface fastener member 50 in which the male engaging elements 52 of water-soluble resin are molded on the substrate sheet 51 is manufactured by, for example, an extrusion molding machine in the following manner. As shown in FIG. 6, as a cylinder 40 having on its peripheral surface a multiplicity of hook-forming cavities 41 rotates in one way in the direction of an arrow, molten water-soluble resin 52$a$ is extruded from a first resin sprue 71 of a die 70 toward the peripheral surface of the cylinder 40 to fill the hook-forming cavities 41. An orifice of the first resin sprue 71 is substantially in contact with the peripheral surface of the cylinder 40. In the meantime, molten synthetic resin 51$a$ of an ordinary kind such as polyamide group, polyester group or polypropylene group is extruded toward the peripheral surface of the cylinder 40 from a second resin sprue 72 which is located in the die 70 under the first resin sprue 71. An orifice of the second resin sprue 72 confronts the peripheral surface of the cylinder 40 with a gap substantially equal to a predetermined thickness of the substrate sheet 51.

When these two kinds of molten resins are simultaneously extruded toward the peripheral surface of the cylinder 40, which is rotating in one direction, the molten water-soluble resin 52$a$ extruded from the first resin sprue 71 is filled directly in the hook-forming cavities 41 and moves successively in the rotating direction of the cylinder 40. During this moving, the molten ordinary resin 51$a$ is extruded from the second resin sprue 72 to fill the gap between the orifice of the second resin sprue 72 and the peripheral surface of the cylinder 40, thus molding the substrate sheet 51 integrally with the hook-shaped male engaging elements 52 in the cavities 41. Then the resulting molded male surface fastener member 50 is cooled as it travels around a substantially half of the peripheral surface of the cylinder 40, whereupon the male surface fastener 50 is drawn from the cylinder 40 by a take-up roller 73.

On the other hand, the fiber male surface fastener member 50 as shown in FIG. 4 is manufactured in the following manner. Firstly, monofilaments for the male engaging elements 52 are prepared by spinning water-soluble resin. They are then woven or knitted in pile form in an ordinary woven or knit cloth simultaneously with weaving or knitting of the cloth according to the conventional method. Whereupon, the individual loop of the monofilaments is cut and then heat-set as hook-shaped engaging elements. Alternatively, with the upper part of the individual loop cut off, the upper end of each cut loop may be fused to form non-illustrated mushroom-shaped engaging element.

Figure 5:
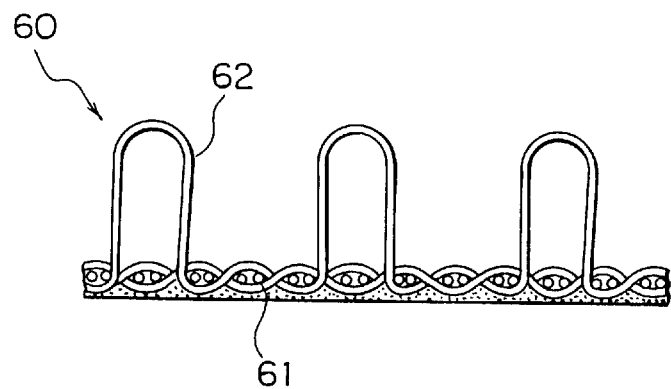
FIG. 5 is a fragmentary cross-sectional view of one example of female surface fastener member to be used in the diaper of FIG. 1, which member is formed of fibers.

The female surface fastener member 60 as mentioned in the above and shown in FIG. 5 is manufactured in the similar manner. Multifilaments or monofilaments of water-soluble resin may be woven or knitted in pile form in a ordinary woven or knit cloth simultaneously with weaving or knitting of the cloth. Note that it is technically difficult to make a non-woven cloth in which only pile fibers standing on the cloth surface are water-soluble resin; consequently, if a non-woven cloth is to be used as the female surface fastener member 60, it is preferable to make the whole cloth of water-soluble resin.

The manner to attach the paper diaper of the illustrated embodiment to the body of the user is as conventional, so its description is omitted here. After use, according to the method of the present invention, the above-described paper diaper can be folded and fastened stably in a compact roll as waste without leakage of excrement, thus making it sanitary to handle the used diaper.

The procedure of a first method of folding and fastening the paper diaper will now be described in detail with reference to FIGS. 7A to 7E.

Figure 7A:
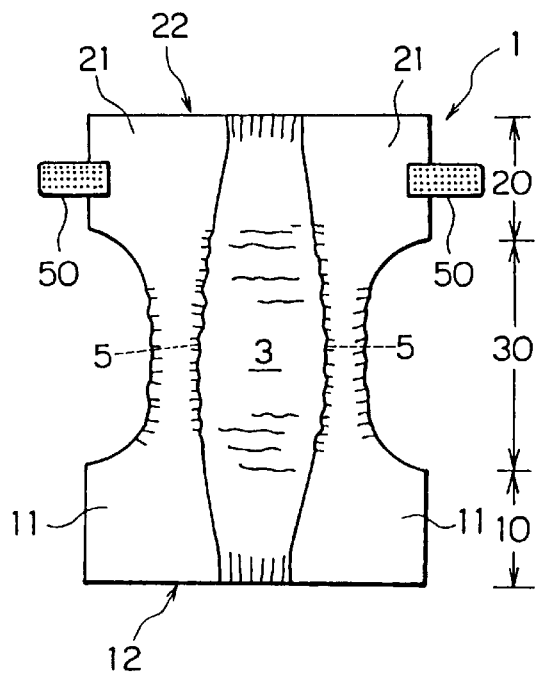
FIGS. 7A to E show the procedure in which the diaper of FIG. 1 is folded and fastened according to the first method.
Figure 7B:
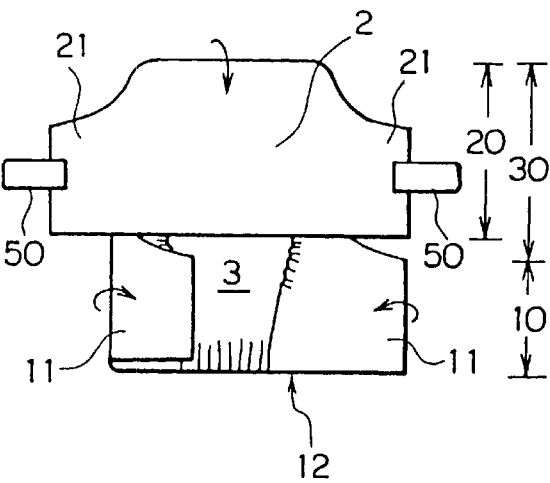
Figure 7C:
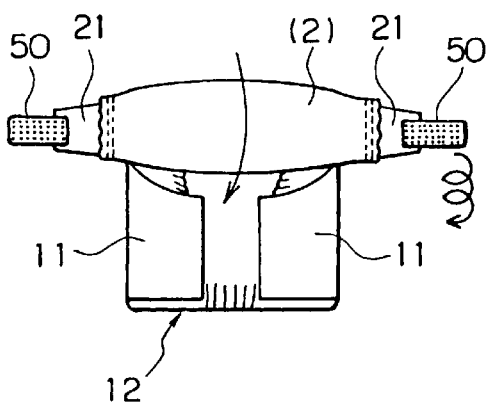
Figure 7D:
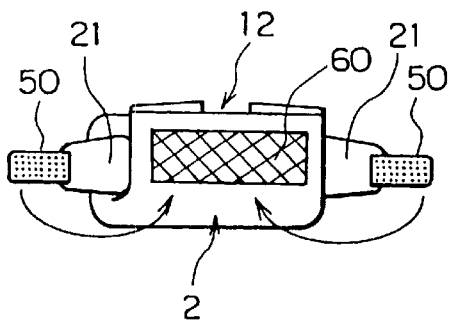

Firstly, the rear flap 20 of the diaper body 1 opened with the top sheet 3 directed upward as shown in FIG. 7A is folded inwardly (downward in the FIG. 7) so as to cover the entire area of the crotch 30 as shown in FIG. 7B. At the same time, the wings 11 of the front flap 10 are folded inwardly. Then the diaper body 1 is wound, with the folded edge of the rear flap 20 as a core, in roll toward the front flap 10 as shown in FIG. 7C. This winding is continued until the second surface fastener member 60 of the front flap 10 comes to the outside of the roll as shown in FIG. 7D. At that time, wing 21 of the rear flap 20 and the two first surface fastener members 50 each having on its front surface a multiplicity of male engaging elements 52 extend laterally in opposite directions from opposite ends of the roll of the diaper body 1.

Then water or alcohol solution is applied or sprayed over the first and/or second surface fastener member 50, 60 whose engaging elements 52, 62 are made of water-soluble resin. As a result, the water-soluble resin dissolves with water or alcohol solution to become adhesive.

Figure 7E:
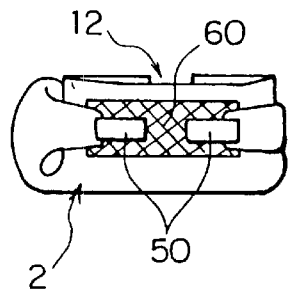

Finally, the opposite male surface fastener members 50 are folded inwardly over the rolled diaper body 1 as indicated by arrows in FIG. 7D and are then pressed against the female surface fastener member 60 as shown in FIGS. 2 and 7E, thus bringing the male engaging elements 52 of each male surface fastener member 50 into engagement with the female engaging elements 62 of the female surface fastener member 60.

The number of windings of the diaper body 1 depends on the amount of excrement existing inside a pair of leak-barrier tapes 5 of the crotch 30.

In the present invention, since the first and second surface fastener members 50, 60 are thus fastened together face to face, it is particularly simple to perform the above-mentioned fastening. Yet since the wings 11, 21 effectively close the opposite ends of the rolled diaper body 1, it is possible to handle the used diaper very sanitarily as waste without leaking the excrement even when it has already moved beyond the leak-barrier tapes 5.

Figure 8:
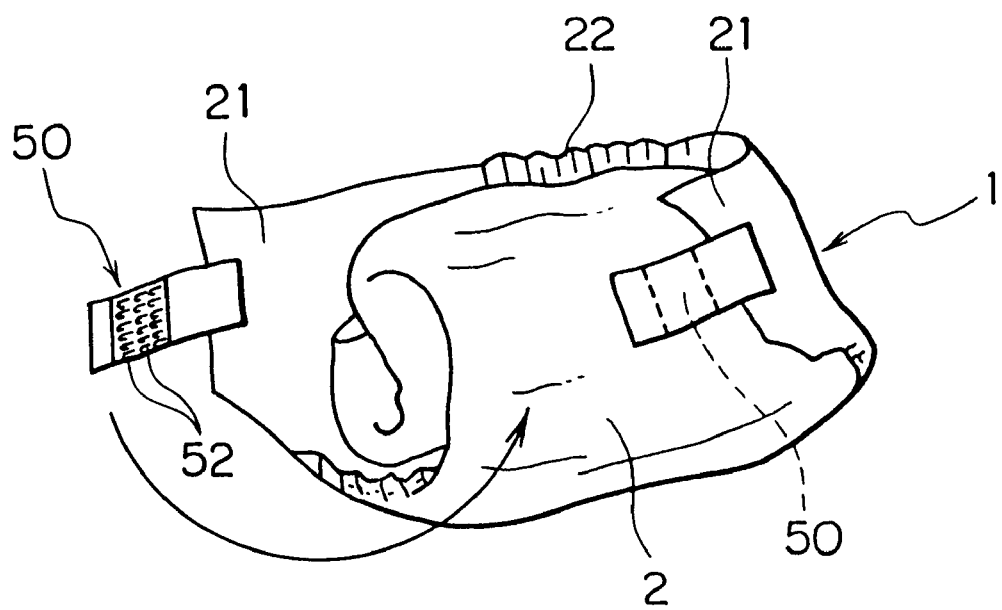
FIG. 8 is a perspective view showing alternative procedure in which the diaper of FIG. 1 is folded and fastened according to a second method.

Although its detail is not shown in the drawings, the disposable diaper of the present invention can be folded and fastened alternatively according to a second method. In the second method, unlike the first method, it is the front flap 10 which is folded inwardly so as to cover the entire area of the crotch 30. The wings 11 of the front flap 10 may be folded inwardly over the front flap 10 before folding the front flap 10. Then the diaper body 1 is wound in roll, with the folded edge of the front flap 20 as a core, toward the rear flap 20. At that time, as shown in FIG.8, the second surface fastener member 60 is completely concealed by the diaper body 1, while the first surface fastener members 50 extend laterally in opposite directions from opposite ends of the folded diaper body 1. Consequently the first surface fastener members 50, in which the water-soluble resin of the engaging elements 52 are dissolved just as the first method, pressed against the exposed surface of the back sheet 2 of the folded diaper body 1, bringing the first surface fastener members 50 in engagement with pile of the back sheet 2.

In the disposable diaper of the foregoing illustrated embodiment, only the engaging elements are made of water-soluble resin. Alternatively, the substrate sheet 51, 61 also may be made of water-soluble resin. As another alternative, other part of the diaper body 1 also may be made of water-soluble resin.

As is apparent from the foregoing description, according to the disposable diaper of the present invention, since the first and second surface fastener members 50, 60 are supported by the front and rear flaps 10, 20, respectively, of the diaper body 1, it is easy to detachably attach the diaper body 1 to the body of the user with adequate fastening strength. Further, since the male and/or female engaging elements 52, 62 of the surface fastener members 50, 60 are made of water-soluble resin, the resin dissolvers with water or alcohol solution to become adhesive to assist in fastening the used diaper roll as waste. As a result, it is possible to handle the used diaper very compactly and sanitarily without losing its roll shape.

It is thus apparent that the present invention should by no means be limited to the illustrated embodiment and various modifications and changes ma be suggested without departing from the scope and spirit of the invention.

What is claimed is:

1. A disposable diaper comprising:

(a) a diaper body having a front flap and a rear flap; and (b) a surface fastener having a pair of first surface fastener members supported by said rear flap and extending laterally in opposite directions from said rear flap and a second surface fastener member supported by said front flap;

(c) each of said first surface fastener members having a first substrate sheet and a multiplicity of first engaging elements standing on a front and/or rear surface of said first substrate sheet;

(d) said second surface fastener member having a second substrate sheet and a multiplicity of second engaging elements standing on a front surface of said second substrate sheet for engagement with said first engaging elements;

(e) said first and/or second engaging elements being made of water-soluble resin and defining an adhesive after application of an amount of a solvent.

2. A disposable diaper according to claim 1, wherein each of said first surface fastener members is a male surface fastener member having male engaging elements and said second surface fastener member is a female surface fastener member having female engaging elements in the form of pile.

3. A disposable diaper according to claim 2, wherein said male engaging elements are integrally molded on said front and/or rear surface of said first substrate sheet made of synthetic resin.

4. A disposable diaper according to claim 2, wherein said male engaging elements are monofilaments integrally woven or knitted in said first substrate sheet of said male surface fastener member.

5. A disposable diaper according to claim 2, wherein said female engaging elements are pile of a woven or knitted cloth substrate sheet of said female surface fastener member.

6. A disposable diaper according to claim 2, wherein said female engaging elements are pile on a front surface of a non-woven cloth substrate sheet of said female surface fastener member.

7. A disposable diaper according to claim 2, wherein said first and/or second substrate sheet is made of water-soluble resin.

8. A disposable diaper according to claim 1 or 7, wherein at least one part of said diaper body is made of water-soluble resin.

9. A disposable diaper according to claim 1, wherein each of said first and second flaps has a pair of lateral wings.

10. A method of folding and fastening a disposable diaper as waste, which diaper includes a diaper body having a front flap and a rear flap, and a surface fastener having a pair of first surface fastener members supported by said rear flap and extending laterally in opposite directions from said rear flap and a second surface fastener member supported by said front flap, each of said first surface fastener members having a first substrate sheet and a multiplicity of first engaging elements standing on a front and/or rear surface of said first substrate sheet, said second surface fastener member having a second substrate sheet and a multiplicity of second engaging elements standing on a front surface of said second substrate sheet for engagement with said first engaging elements, said first and/or second engaging elements being made of water-soluble resin, the method comprising steps of:

(a) folding approximately ⅓ to ⅖ of said diaper body on the side of said rear flap inwardly;

(b) winding said diaper body into a roll with said folded rear flap as a core toward said front flap;

(c) dissolving at least a portion of said water-soluble resin of said first engaging elements of said first surface fastener members projecting from opposite ends of said roll of said diaper body and/or said second engaging elements of said second surface fastener member with an amount of water to form an adhesive from the dissolved portion of said front and/or second engaging elements; and (d) pressing said first surface fastener members against said second surface fastener member to fasten said diaper body in roll with said adhesive.

11. A method of folding a fastening a disposable diaper as waste, which diaper includes a diaper body having a front flap and a rear flap, and a surface fastener having a pair of first surface fastener members supported by said rear flap and extending laterally in opposite directions from said rear flap and a second surface fastener member supported by said front flap, each of said first surface fastener members having a first substrate sheet and a multiplicity of first engaging elements standing on a front and/or rear surface of said first substrate sheet, said second surface fastener member having a second substrate sheet and a multiplicity of second engaging elements standing on a front surface of said second substrate sheet for engagement with said first engaging elements, said first and/or second engaging elements being made of water-soluble resin, the method comprising steps of:

(a) folding approximately ⅓ to ⅖ of said diaper body on the side of said front flap inwardly;

(b) winding said diaper body into a roll with said folded front flap as a core toward said rear flap;

(c) dissolving at least a portion of said water-soluble resin of said first engaging elements of said first surface fastener members projecting from opposite ends of said roll of said diaper body with an amount of water to form an adhesive from the dissolved portion of said first engaging elements; and (d) pressing said first surface fastener members against a outer sheet of said diaper body to fasten said diaper body in roll with said adhesive.

* * * * *